(12) United States Patent
Kumano et al.

(10) Patent No.: US 10,132,819 B2
(45) Date of Patent: Nov. 20, 2018

(54) METHOD FOR MEASURING CLOTTING TIME, MEASUREMENT DEVICE FOR CLOTTING TIME, AND REAGENT KIT

(71) Applicants: SYSMEX CORPORATION, Kobe-shi, Hyogo (JP); SCHOOL JURIDICAL PERSON HIGASHI-NIPPON-GAKUEN, Ishikari-gun, Hokkaido (JP)

(72) Inventors: Osamu Kumano, Kobe (JP); Haruki Yamaguchi, Kobe (JP); Takeshi Suzuki, Kobe (JP); Masahiro Ieko, Ishikari-gun (JP)

(73) Assignees: SYSMEX CORPORATION, Kobe-shi, Hyogo (JP); SCHOOL JURIDICAL PERSON HIGASHI-NIPPON-GAKUEN, Ishikari-gun, Hokkaido (JP)

( * ) Notice: Subject to any disclaimer, the term of this patent is extended or adjusted under 35 U.S.C. 154(b) by 154 days.

(21) Appl. No.: 15/219,456

(22) Filed: Jul. 26, 2016

(65) Prior Publication Data

US 2017/0030933 A1 Feb. 2, 2017

(30) Foreign Application Priority Data

Jul. 30, 2015 (JP) ................................. 2015-150779

(51) Int. Cl.
*G01N 33/86* (2006.01)
*G01N 33/48* (2006.01)
(Continued)

(52) U.S. Cl.
CPC ............ *G01N 33/86* (2013.01); *G01N 21/82* (2013.01); *G01N 33/4905* (2013.01); *G01N 2405/04* (2013.01); *G01N 2800/224* (2013.01)

(58) Field of Classification Search
CPC .... G01N 33/49; G01N 33/4905; G01N 33/86; G01N 21/82; G01N 2405/04; G01N 2800/224
(Continued)

(56) References Cited

U.S. PATENT DOCUMENTS 5,055,412 A * 10/1991 Proksch ................. G01N 33/86
435/13
5,550,028 A * 8/1996 Lee ......................... G01N 33/86
435/13
(Continued)

FOREIGN PATENT DOCUMENTS

EP   0 107 383 A1   5/1984
EP   0 947 585 A1   10/1999
(Continued)

OTHER PUBLICATIONS

Extended European Search Report dated Nov. 16, 2016, from the European Patent Office in corresponding European application No. 16181818.2.
(Continued)

*Primary Examiner* — Maureen Wallenhorst
(74) *Attorney, Agent, or Firm* — Sughrue Mion, PLLC

(57) ABSTRACT

Disclosed is a method for measuring a clotting time, including:
a mixing step of mixing a blood sample, an activator, a phospholipid, and a manganese ion-forming compound to obtain a specimen; and
a measurement step of mixing the specimen obtained in the mixing step with a calcium salt to prepare a measurement specimen and measuring the clotting time of the measurement specimen,
wherein the blood sample is mixed with the manganese ion-forming compound separately from the activator and the phospholipid in the mixing step.

13 Claims, 8 Drawing Sheets

(51) Int. Cl.
*G01N 21/82* (2006.01)
*G01N 33/49* (2006.01)

(58) Field of Classification Search
USPC ....... 436/63, 69, 71, 73, 84; 422/73; 435/13; 73/64.41; 600/369
See application file for complete search history.

(56) References Cited

U.S. PATENT DOCUMENTS

| | | | |
|---|---|---|---|
| 8,557,592 B2* | 10/2013 | Okuda | G01N 33/564 422/430 |
| 8,759,108 B2* | 6/2014 | Okuda | G01N 33/86 422/430 |
| 9,835,635 B2* | 12/2017 | Kumano | G01N 33/86 |
| 2003/0157582 A1 | 8/2003 | Roisin et al. | |

FOREIGN PATENT DOCUMENTS

| | | |
|---|---|---|
| EP | 2 423 687 A2 | 2/2012 |
| WO | 90/11368 A1 | 10/1990 |

OTHER PUBLICATIONS

"Activated partial thromboplastin time kit", PTT LA reagent "RD", Package Insert, Revised Dec. 2012 (third edition), 8 pages.

* cited by examiner

METHOD FOR MEASURING CLOTTING TIME, MEASUREMENT DEVICE FOR CLOTTING TIME, AND REAGENT KIT

CROSS REFERENCE TO RELATED APPLICATIONS

This application claims priority from prior Japanese Patent Application No. 2015-150779, filed on Jul. 30, 2015, entitled "METHOD FOR MEASURING CLOTTING TIME, MEASUREMENT DEVICE FOR CLOTTING TIME, CLOTTING TIME MEASURING REAGENT, AND REAGENT KIT", the entire contents of which are incorporated herein by reference.

TECHNICAL FIELD

The present invention relates to a method for measuring a clotting time, a measurement device for a clotting time, a clotting time measuring reagent, and a reagent kit.

BACKGROUND

In order to examine the presence of abnormalities in blood-clotting factors, a blood clotting test is performed as a clinical test. In the blood clotting test, for example, prolongation of activated partial thromboplastin time is used as an indicator of abnormalities in blood-clotting factors. The prolongation of activated partial thromboplastin time is assumed to be due to lupus anticoagulant or the like.

In the lupus anticoagulant screening test, a method of using a reagent containing a low level of phospholipids is performed. The use of the reagent containing a low level of phospholipids easily causes an inhibitory reaction on the phospholipids due to lupus anticoagulant. Therefore, this method allows the prolongation of clotting time caused by lupus anticoagulant to be easily detected. There is a reagent for detecting lupus anticoagulant such as an activated partial thromboplastin time kit PTT LA reagent "RD" Package Insert, Revised December, 2012 (third edition), [online], [searched on Jul. 28, 2015], Internet <URL:http://www.info.pmda.go.jp/downfiles/ivd/PDF/700025_21700AMY00198000_A_01_02. pdf> (Non-Patent Literature 1).

The clotting time in the case of measurement of normal plasma as a specimen using the reagent described in Non Patent Literature 1 is in the range of 29 to 43 seconds. This clotting time is longer than the clotting time in the case of measurement using a usual reagent for measuring activated partial thromboplastin time which is not a reagent for detecting lupus anticoagulant. Accordingly, it is desirable to prevent the clotting time from becoming too long.

SUMMARY OF THE INVENTION

The scope of the present invention is defined solely by the appended claims, and is not affected to any degree by the statements within this summary.

A first aspect of the present invention includes a method for measuring a clotting time, including:

a mixing step of mixing a blood sample, an activator, a phospholipid, and a manganese ion-forming compound to obtain a specimen; and a measurement step of mixing the specimen obtained in the mixing step with a calcium salt to prepare a measurement specimen and measuring the clotting time of the measurement specimen, wherein the blood sample is mixed with the manganese ion-forming compound separately from the activator and the phospholipid in the mixing step.

A second aspect of the present invention includes a measurement device for a clotting time, including a specimen preparing section that mixes a blood sample, an activator, a phospholipid, and a manganese ion-forming compound to prepare a specimen, and mixes the obtained specimen with a calcium salt to obtain a measurement specimen; a detection unit that obtains clotting information showing a change associated with a clotting reaction from the measurement specimen obtained in the specimen preparing section; a calculator that calculates the clotting time of the measurement specimen based on the clotting information obtained by the detection unit; and a reagent accommodating portion that accommodates an activator, a phospholipid, a manganese ion-forming compound, and a calcium salt; wherein the specimen preparing section obtains the activator, the phospholipid, and the manganese ion-forming compound from the reagent accommodating portion, and mixes the blood sample with the manganese ion-forming compound separately from the activator and the phospholipid to prepare a specimen, and the specimen preparing section obtains the calcium salt from the reagent accommodating portion, and mixes the calcium salt with the specimen to obtain a measurement specimen.

A third aspect of the present invention includes a clotting time measuring reagent that is used in the method for measuring a clotting time, which contains a manganese ion-forming compound.

A fourth aspect of the present invention includes a reagent kit including a first reagent containing an activator and a phospholipid accommodated in a first reagent container, a second reagent containing a manganese ion-forming compound accommodated in a second reagent container, and a third reagent containing a calcium salt accommodated in a third reagent container.

DETAILED DESCRIPTION OF THE PREFERRED EMBODIMENTS

1. Method for Measuring Clotting Time

Figure 1:
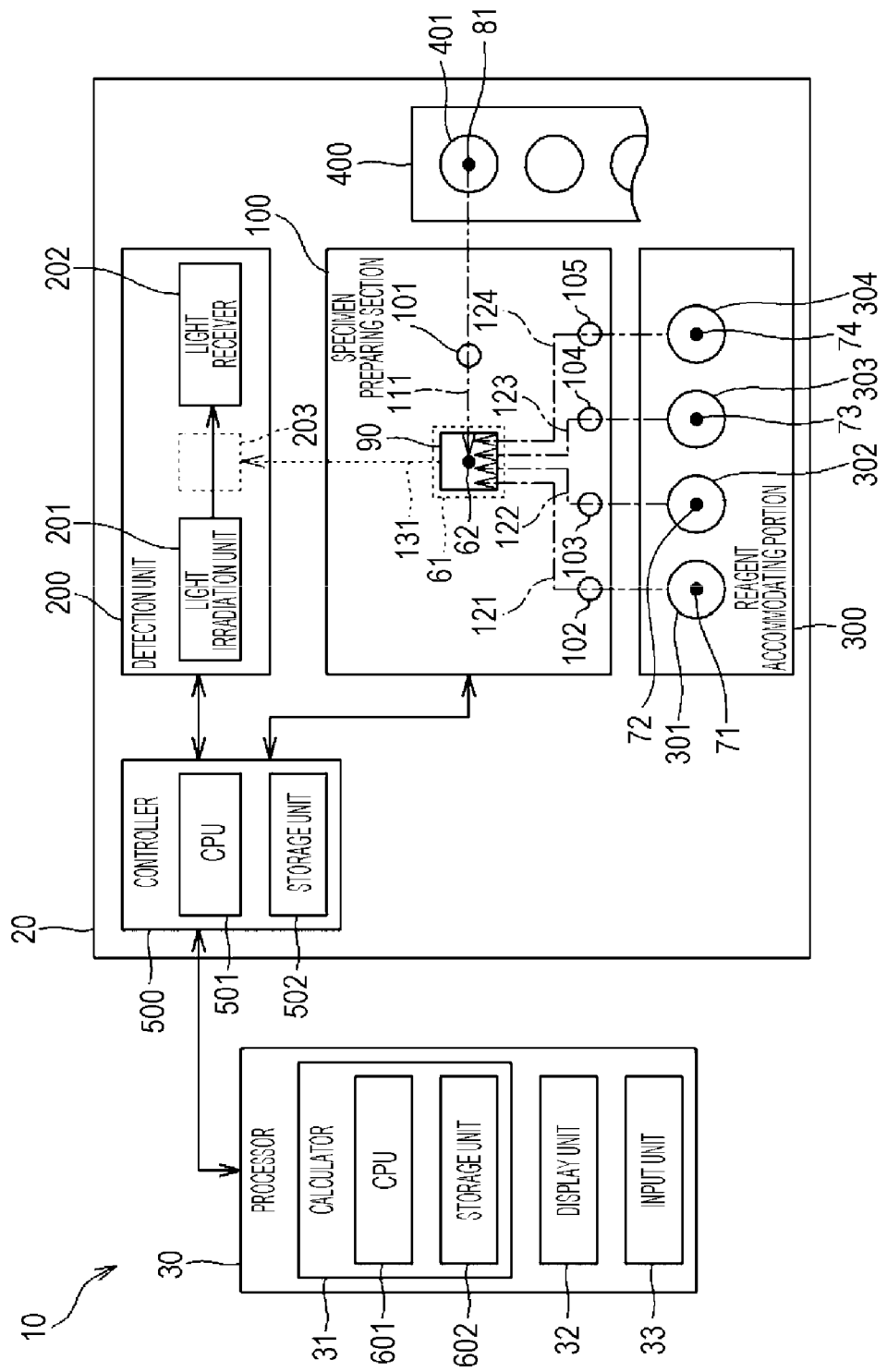
FIG. 1 is a configuration diagram of a measurement device for a clotting time.

The method for measuring a clotting time according to an embodiment (hereinafter simply referred to as "measurement method") includes:

a mixing step of mixing a blood sample, an activator, a phospholipid, and a manganese ion-forming compound to obtain a specimen; and a measurement step of mixing the specimen obtained in the mixing step with a calcium salt to prepare a measurement specimen and measuring the clotting time of the measurement specimen.

In the method, the blood sample is mixed with the manganese ion-forming compound separately from the activator and the phospholipid in the mixing step. In the measurement method according to the embodiment, the blood sample is mixed with the manganese ion-forming compound separately from the activator and phospholipid in the mixing step. Therefore, the measurement method according to the embodiment can prevent the clotting time from becoming too long during the measurement of clotting time.

The term "specimen" used herein means a mixture of a blood sample, an activator, a phospholipid, and a manganese ion-forming compound. The term "measurement specimen" means a mixture of a blood sample, an activator, a phospholipid, a manganese ion-forming compound, and a calcium salt.

Examples of the blood sample include plasma, but are not particularly limited thereto. The term "test plasma" used herein means plasma obtained from a subject. The term "normal plasma" used herein means plasma obtained from blood of a healthy individual. The normal plasma may be commercially available normal plasma.

The activator should be a substance having an effect of activating contact factors involved in the intrinsic coagulation pathway. Examples of the contact factors include prekallikrein, high-molecular-weight kininogen, and factors XII and XI, but are not particularly limited thereto. Examples of the activator include ellagic acid compounds, silica, kaolin, diatomaceous earth (e.g. product name: Celite (registered trademark), manufactured by Celite Corporation), but are not particularly limited thereto. These activators may be used singly, or as a mixture of two or more kinds thereof. The term "ellagic acid compound" means a concept including ellagic acid, and a salt and a metal complex of ellagic acid.

A phospholipid accelerates a blood clotting reaction. The phospholipid is a lipid having a phosphoric ester site in a molecular structure. The phospholipid may be a naturally occurring or synthetic phospholipid. Examples of the naturally occurring phospholipid include phospholipids derived from animals such as rabbit, bovine, porcine, chicken, and human; and phospholipids derived from plants such as soybean, but are not limited thereto. Examples of the phospholipids derived from animals include phospholipids derived from rabbit brain, bovine brain, yolk, human placenta, and the like, but are not limited thereto. Specific examples of the phospholipid include glycerophospholipids such as phosphatidylethanolamine, phosphatidylcholine, and phosphatidylserine, but are not limited thereto. Among these phospholipids, phosphatidylethanolamine, phosphatidylcholine, and phosphatidylserine are preferred from the viewpoint of efficient progression of the blood clotting reaction. These phospholipids may be used singly, or as a mixture of two or more kinds thereof. Examples of the fatty acid side chains in phospholipids include palmitoyl, oleoyl, and stearoyl groups, but are not particularly limited thereto. These fatty acid side chains may be appropriately selected as long as the blood clotting reaction is not hindered.

The manganese ion-forming compound should be a compound that forms manganese ions in a blood sample. The manganese ion-forming compound is preferably a compound that forms divalent ions. Examples of the manganese ion-forming compound include manganese chloride, potassium permanganate, manganese sulfate, manganese nitrate, and manganese acetate, but are not particularly limited thereto. Among these manganese ion-forming compounds, manganese chloride is preferred. These manganese ion-forming compounds may be used singly, or as a mixture of two or more kinds thereof.

The calcium salt should be a salt that forms calcium ions in a measurement specimen. Examples of the calcium salt include calcium chloride, calcium sulfate, calcium nitrite, calcium carbonate, calcium lactate, and calcium tartrate, but are not particularly limited thereto. These calcium salts may be used singly, or as a mixture of two or more kinds thereof.

The measurement method according to the embodiment includes the following aspects:

(Aspect 1) a method of mixing a blood sample, an activator, and a phospholipid, and adding a manganese ion-forming compound thereto; and (Aspect 2) a method of mixing a blood sample with a manganese ion-forming compound, and adding an activator and a phospholipid thereto.

Hereinafter, the measurement method according to the embodiment will be described with reference to Aspect 1, but is not particularly limited thereto. In the method of Aspect 1, the mixing step includes:

(A) mixing the blood sample, the activator, and the phospholipid to obtain a mixture; and (B) mixing the mixture with the manganese ion-forming compound.

Prior to step (A), the blood sample may be heated to a temperature appropriate for performing the clotting reaction. Usually, the heating temperature of the blood sample is preferably from 30 to 45° C. and more preferably from 36 to 38° C.

In step (A), the blood sample, the activator, and the phospholipid are mixed to obtain a mixture. The order of mixing the blood sample, the activator, and the phospholipid is not particularly limited. The activator and phospholipid may be mixed simultaneously with the blood sample. The activator and phospholipid may be mixed with the blood sample at different times. In this case, the phospholipid may be added after the activator is added to the blood sample, or alternatively, the activator may be added after the phospholipid is added to the blood sample.

In step (A), the amount of the activator to be mixed with the blood sample should be an amount at which the concentration of the activator in the measurement specimen is a predetermined concentration. The concentration of the activator in the measurement specimen may be appropriately set depending on the type of activator. When the activator is an ellagic acid compound, usually, the concentration of the activator in the measurement specimen is preferably from 3.5 to 150 μM and more preferably from 10 to 50 μM. When the activator is silica, usually, the concentration of the activator in the measurement specimen is preferably from 0.04 to 0.4 mg/mL and more preferably from 0.07 to 0.2 mg/mL.

In step (A1), the amount of the phospholipid to be mixed with the blood sample should be an amount at which the concentration of the phospholipid in the measurement specimen is a predetermined concentration. The concentration of the phospholipid in the measurement specimen may be appropriately set depending on the type of phospholipid. When the phospholipid is phosphatidylethanolamine, usually, the concentration of the phospholipid in the measurement specimen is preferably from 1 to 150 μg/mL and more preferably from 5 to 50 μg/mL. When the phospholipid is phosphatidylcholine, usually, the concentration of the phospholipid in the measurement specimen is preferably from 1 to 100 µg/mL and more preferably from 5 to 80 µg/mL. When the phospholipid is phosphatidylserine, usually, the concentration of the phospholipid in the measurement specimen is preferably from 0.1 to 50 µg/mL and more preferably from 1 to 10 µg/mL. When the phospholipid is a mixture of two or more kinds of phospholipids, usually, the concentration of each of the phospholipids in the measurement specimen is preferably from 5 to 400 µg/mL and more preferably from 20 to 100 µg/mL.

The heating temperature when mixing the blood sample, the activator and/or the phospholipid should be a temperature appropriate for performing the blood clotting reaction. Usually, the heating temperature is preferably from 30 to 45° C. and more preferably from 36 to 38° C. Usually, the heating time is preferably from 10 to 150 seconds and more preferably from 30 to 90 seconds.

In step (B), the mixture obtained in step (A) is mixed with a manganese ion-forming compound to obtain a specimen.

In step (B), the amount of the manganese ion-forming compound to be mixed with the mixture obtained in step (A) should be an amount at which the final concentration of the manganese ion-forming compound in the measurement specimen is a predetermined concentration. The final concentration of the manganese ion-forming compound in the measurement specimen is preferably 0.1 µM or more, more preferably 0.1 mM or more, and preferably less than 10 mM and more preferably 5 mM or less.

The heating temperature when mixing the mixture obtained in step (A) with the manganese ion-forming compound should be a temperature appropriate for performing the blood clotting reaction. Usually, the temperature is preferably from 30 to 45° C. and more preferably from 36 to 38° C. Usually, the heating time is preferably from 30 to 420 seconds and more preferably from 100 to 350 seconds.

From the viewpoint of effectively preventing the clotting time from becoming too long during the measurement of clotting time, the mixture is preferably mixed with a manganese ion-forming compound in step (B) within 150 seconds, preferably within 60 seconds after the end of mixing the blood sample, the activator, and the phospholipid in step (A).

In the measurement step, the specimen obtained in the mixing step is mixed with a calcium salt to prepare a measurement specimen, and the clotting time of the measurement specimen is measured.

The amount of the calcium salt to be mixed with the specimen should be an amount at which the concentration of the calcium salt in the measurement specimen is a predetermined concentration. The concentration of calcium salt in the measurement specimen is preferably from 2 to 20 mM and more preferably from 4 to 10 mM.

In the measurement step, the specimen may be heated to an appropriate temperature to carry out a clotting reaction before mixing the specimen with the calcium salt. The heating temperature of the specimen is preferably 30° C. or more and more preferably 36° C. or more from the viewpoint of reactivity in the clotting reaction. The heating temperature of the specimen is preferably 45° C. or less and more preferably 38° C. or less from the viewpoint of protein stability. In this case, the heating time is preferably 1 minute or more and more preferably 2 minutes or more from the viewpoint of reactivity in the clotting reaction. The heating time is preferably 6 minutes or less and more preferably 5 minutes or less from the viewpoint of protein stability.

The clotting time of the measurement specimen can be examined based on clotting information. Examples of the clotting information include changes in the transmitted or scattered light when the measurement specimen is irradiated with light and changes in the viscosity of the measurement specimen, but are not particularly limited thereto. In this case, the clotting time of the measurement specimen can be examined by emitting light to the measurement specimen, and monitoring changes in the transmitted light passed through the measurement specimen or the scattered light from the measurement specimen, or monitoring changes in the viscosity of the measurement specimen. The term "clotting time" used herein means an activated partial thromboplastin time. The clotting time is a time from when the mixing of the specimen with the calcium salt starts till when the plasma clots.

The clotting of plasma can be determined using as an indicator, for example, the fact that the light from the measurement specimen irradiated with light does not change any more, or the fact that the viscosity of the measurement specimen does not change any more.

2. Measurement Device for Clotting Time

[Overall Configuration of Measurement Device]

An example of the measurement device for a clotting time (hereinafter, simply referred to as "measurement device") to be used for the measurement method as described above will be described with reference to the attached drawings. As shown in FIG. 1, a measurement device 10 includes a measurement unit 20 and a processing apparatus 30. The measurement unit 20 and the processing apparatus 30 are communicably connected to each other.

[Configuration of Measurement Unit]

As shown in FIG. 1, the measurement unit 20 includes a specimen preparing section 100, a detection unit 200, and a reagent accommodating portion 300, a sample accommodating portion 400 accommodating a blood sample, and a controller 500.

The specimen preparing section 100 obtains a reagent from the reagent accommodating portion 300 and also obtains a blood sample from the sample accommodating portion 400. The specimen preparing section 100 mixes the obtained reagent with the obtained blood sample based on a predetermined procedure to prepare a measurement specimen. The specimen preparing section 100 includes a sample transporting section 111, a first reagent transporting section 112, a second reagent transporting section 113, a third reagent transporting section 114, a fourth reagent transporting section 115, and a cuvette transporting section 131. The sample transporting section 111 has a first nozzle 101. The sample transporting section 111 obtains a blood sample accommodated in the sample accommodating portion 400. The sample transporting section 111 discharges the obtained blood sample into a cuvette 90. The first reagent transporting section 112 has a second nozzle 102. The first reagent transporting section 112 obtains a reagent accommodated in a first container 301 of the reagent accommodating portion 300 through the second nozzle 102. The first reagent transporting section 112 discharges the obtained reagent into the cuvette 90. The second reagent transporting section 113 has a third nozzle 103. The second reagent transporting section 113 obtains a reagent accommodated in a second container 302 of the reagent accommodating portion 300 through the third nozzle 103. The second reagent transporting section 113 discharges the obtained reagent into the cuvette 90. The third reagent transporting section 114 obtains a reagent accommodated in a third container 303 of the reagent accommodating portion 300 through a fourth nozzle 104. The third reagent transporting section 114 discharges the obtained reagent into the cuvette 90. The fourth reagent transporting section 115 obtains a reagent accommodated in a fourth container 304 of the reagent accommodating portion 300 through a fifth nozzle 105. The fourth reagent transporting section 115 discharges the obtained reagent into the cuvette 90. The cuvette transporting section 131 transports the cuvette 90 accommodating a prepared measurement specimen to the detection unit 200.

The detection unit 200 includes a light irradiation unit 201, a light receiver 202, and a second cuvette mounting portion 203. The light irradiation unit 201 has a light source of light emitted to a measurement specimen. The wavelength of emitted light should be a wavelength suitable for monitoring the change with the progress of the clotting reaction of blood. The light receiver 202 receives light from the measurement specimen. The light from the measurement specimen may be transmitted or scattered light. The light receiver 202 outputs an electric signal corresponding to the amount of the received light to a calculator 31 of the processing apparatus. The second cuvette mounting portion 203 is provided between the light irradiation unit 201 and the light receiver 202. The cuvette 90 transported from the specimen preparing section 100 is placed in the second cuvette mounting portion 203.

The reagent accommodating portion 300 accommodates a reagent used for measurement of clotting time. In the embodiment, the reagent accommodating portion 300 includes a first container 301 that accommodates an activator, a second container 302 that accommodates a phospholipid, a third container 303 that accommodates a manganese ion-forming compound, and a fourth container 304 that accommodates a calcium salt. An identifier for identifying the kind of reagent accommodated in the container is provided in each of the first to fourth containers. Examples of the identifiers include bar codes, but are not particularly limited thereto. In the embodiment, the first container 301 and the second container 302 as different containers are provided in the reagent accommodating portion 300. However, since the activator and phospholipid may be simultaneously mixed with a blood sample, the activator and phospholipid may be accommodated in one common container in place of the first and second containers. In this case, the first reagent transporting section 112 and the second reagent transporting section 113 are one common transporting section.

The sample accommodating portion 400 accommodates a blood sample. In the embodiment, the sample accommodating portion 400 includes a plurality of sample containers 401. The sample accommodating portion 400 transports the sample containers 401 accommodating desired blood samples to a predetermined sample aspirating position. Identifiers for identifying the kinds of blood samples accommodated in the containers are provided in the sample containers 401. Examples of the identifiers include bar codes, but are not particularly limited thereto.

The controller 500 includes a central processing unit (CPU) 501 and a storage unit 502. The controller 500 is composed of a computer. The CPU 501 executes the computer program stored in the storage unit 502. Thus, the CPU 501 prepares the specimen in the specimen preparing section 100 and provides optical information on a measurement specimen in the detection unit 200. Examples of the computer program include a computer program for preparing a measurement specimen and a computer program for providing optical information on the measurement specimen, but are not particularly limited thereto. The storage unit 502 further stores reagent identification information to identify a reagent accommodated in the reagent accommodating portion 300, specimen preparation information on procedures in preparing a measurement specimen, and sample identification information to identify a blood sample accommodated in the sample accommodating portion 400. Examples of the reagent identification information include information on association of the type of reagent, the position of accommodating containers, and identifiers, but are not particularly limited thereto. Examples of the sample identification information include information on association of the type of blood sample, the position of accommodating containers, and identifiers, but are not particularly limited thereto. The CPU 501 executes the computer program for preparing a measurement specimen using the reagent identification information and specimen preparation information stored in the storage unit 502. Thus, the CPU 501 makes the specimen preparing section 100 of the measurement unit 20 prepare the measurement specimen.

[Configuration of Processing Apparatus]

As shown in FIG. 1, the processing apparatus 30 includes a calculator 31, a display unit 32, and an input unit 33. In the embodiment, the processing apparatus 30 is composed of a computer system. The calculator 31 includes a CPU 601 and a storage unit 602. The CPU 601 executes the computer program stored in the storage unit 602. Thus, the CPU 601 calculates clotting time. Examples of the display unit 32 include screen displays, but are not particularly limited thereto. The display unit 32 displays, for example, information on the calculated clotting time. Examples of the input unit 33 include keyboards and mice, but are not particularly limited thereto.

The storage unit 602 is installed with computer programs to be executed by the CPU 601, such as an operating system and an application program, as well as data used in executing the computer programs. Examples of the application program include computer programs for measuring the clotting time, but are not particularly limited thereto. The CPU 601 executes the computer program to measure clotting time stored in the storage unit 602. Thus, the CPU 601 makes the measurement device 10 measure clotting time.

[Modification of Measurement Device]

The sample transporting section 111, the first reagent transporting section 112, the second reagent transporting section 113, the third reagent transporting section 114, and the fourth reagent transporting section 115 may each be a flow path for flowing a sample or reagent. Examples of the flow paths include tubes, but are not particularly limited thereto.

The clotting time may be measured based on the increase in the viscosity due to blood clotting and other clotting information. When the clotting time is measured based on the increase in the viscosity due to blood clotting, the detection unit 200 includes a high frequency transmitting coil, a high frequency receiving coil, a cuvette mounting portion which is located between the high frequency transmitting coil and the high frequency receiving coil on which a cuvette accommodating a steel ball is mounted, and electromagnets provided at both ends of the cuvette mounting portion. The steel ball in the cuvette vibrates from side to side due to the magnetism generated by the electromagnets. The amplitude of vibration decreases as the viscosity increases. When the clotting of the measurement specimen starts, the viscosity of the measurement specimen increases, whereby the amplitude of the steel ball decreases. Therefore, the detection unit 200 detects changes in amplitude based on reception of a high-frequency wave transmitted by the high frequency transmitting coil by a high frequency receiving coil. The calculator 31 of the processing apparatus 30 calculates clotting time based on the detected changes in amplitude.

[Procedure of Measuring Clotting Time by Measurement Device]

Subsequently, an overview of a procedure of measuring the clotting time by the measurement device 10 will be described with reference to FIG. 2. In the following procedure, the controller 500 of the measurement unit 20 executes the computer program for preparing a measurement specimen which is stored in the storage unit 502 using the reagent identification information and specimen preparation information obtained from the storage unit 502. The controller 500 executes the computer program for providing optical information on the measurement specimen which is stored in the storage unit 502. The calculator 31 of the processing apparatus 30 executes the computer program for measuring the clotting time which is stored in the storage unit 602 using the obtained optical information.

In step S1, the controller 500 of the measurement unit 20 makes the specimen preparing section 100 prepare a specimen. The specimen preparation in step S1 is executed in accordance with the following procedures shown in FIGS. 3 and 4.

Thereafter, in step S2, the controller 500 makes the specimen preparing section 100 add a calcium salt to the specimen. In step S3, the controller 500 makes the detection unit 200 provide optical information on the measurement specimen. The addition of the calcium salt to the specimen in step S2 and the provision of the optical information in step S3 are executed in accordance with the procedure shown in FIG. 5.

Thereafter, in step S4, the calculator 31 of the processing apparatus 30 executes a computer program for calculating clotting time to calculate the clotting time.

[Procedure of Preparing Specimen]

Figure 3:
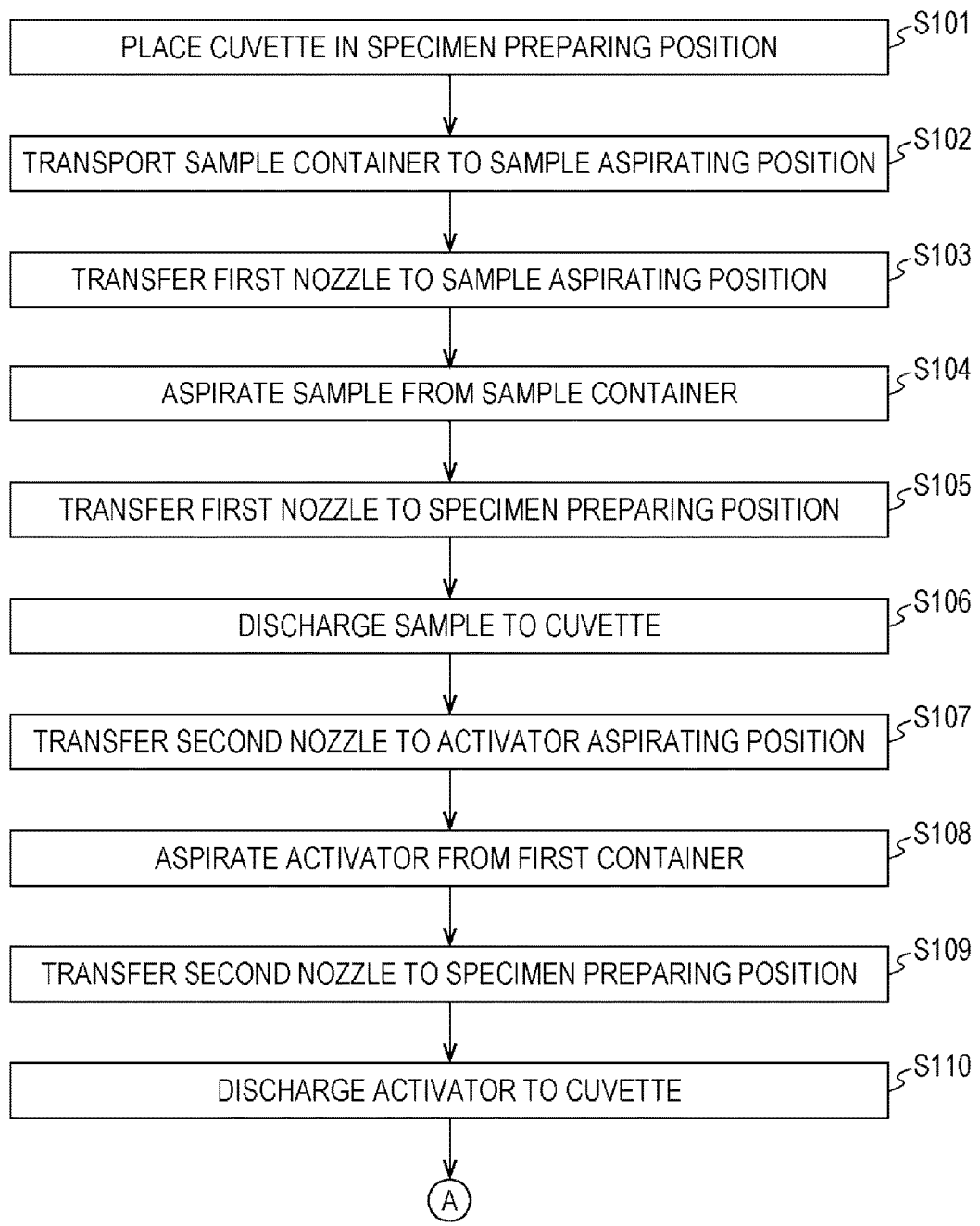
FIG. 3 is a flow chart showing a procedure of preparing a specimen.

Subsequently, an overview of a procedure of preparing a specimen by the measurement device 10 will be described with reference to FIGS. 3 and 4.

In Step S101, the controller 500 first makes the specimen preparing section 100 place the cuvette 90 in a specimen preparing position 62 in FIG. 1. Specifically, the controller 500 makes the specimen preparing section 100 mount the cuvette 90 in a first cuvette mounting portion 61 in FIG. 1. Thus, the cuvette 90 is placed in the specimen preparing position 62.

Then, in step S102, the controller 500 makes the sample accommodating portion 400 transport the sample container 401 to the sample aspirating position 81 in FIG. 1. At this time, the controller 500 makes the sample accommodating portion 400 select a sample container 401 accommodating a desired blood sample based on the sample identification information stored in the storage unit 502. Then, the controller makes the sample accommodating portion 400 transport the selected sample container 401 so as to be located in the sample aspirating position 81.

Then, in step S103, the controller 500 makes the specimen preparing section 100 transfer the first nozzle 101 to the sample aspirating position 81. Thereafter, in step S104, the controller 500 makes the specimen preparing section 100 aspirate the blood sample from the sample container 401. Specifically, the controller 500 makes the specimen preparing section 100 aspirate the blood sample accommodated in the sample container 401 through the first nozzle 101.

Then, in step S105, the controller 500 makes the specimen preparing section 100 transfer the first nozzle 101 to the specimen preparing position 62. Thereafter, in step S106, the controller 500 makes the specimen preparing section 100 discharge the blood sample to the cuvette 90. Specifically, the controller 500 makes the specimen preparing section 100 discharge the blood sample aspirated by the first nozzle 101 to the cuvette 90.

Then, in step S107, the controller 500 makes the specimen preparing section 100 transfer the second nozzle 102 to an activator aspirating position 71. Thereafter, in step S108, the controller 500 makes the specimen preparing section 100 aspirate an activator from the first container 301. Specifically, the controller 500 makes the specimen preparing section 100 aspirate the activator accommodated in the first container 301 through the second nozzle 102.

Then, in step S109, the controller 500 makes the specimen preparing section 100 transfer the second nozzle 102 to the specimen preparing position 62. Thereafter, in step S110, the controller 500 makes the specimen preparing section 100 discharge the activator to the cuvette 90. Specifically, the controller 500 makes the specimen preparing section 100 discharge the activator aspirated through the second nozzle 102 to the cuvette 90.

Figure 4:
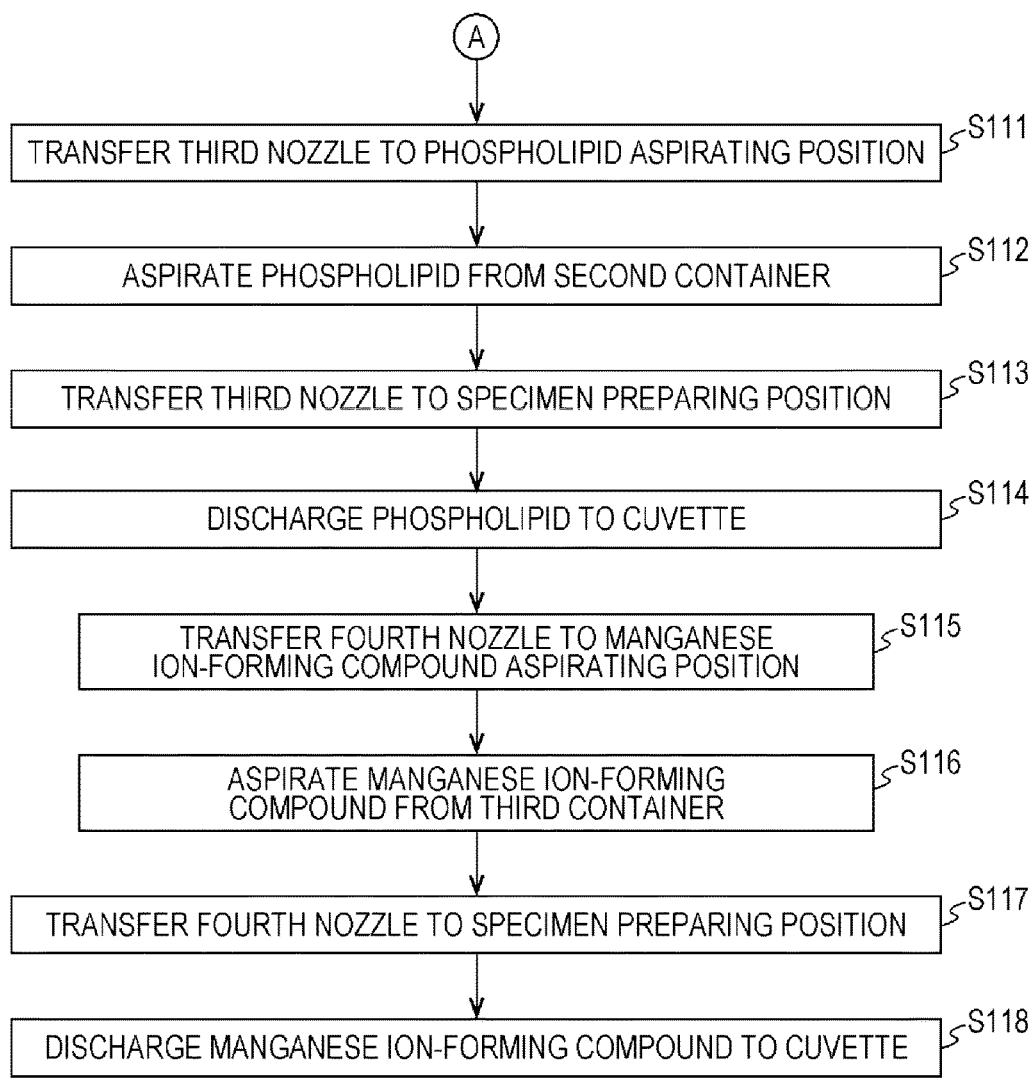
FIG. 4 is a flow chart showing a procedure of preparing a specimen.

Then, in Steps S111 to S114 of FIG. 4, the controller 500 makes the specimen preparing section 100 transfer the third nozzle 103 to the phospholipid aspirating position 72, aspirate a phospholipid from the second container 302, transfer the third nozzle 103 to the specimen preparing position 62, and discharge the phospholipid to the cuvette 90, respectively. Steps S111 to S114 are respectively the same as Steps S107 to S110 of FIG. 3 except for a series of operations including aspirating and discharging the phospholipid through the third nozzle 103.

Then, in Steps S115 to S118, the controller 500 makes the specimen preparing section 100 transfer the fourth nozzle 104 to a manganese ion-forming compound aspirating position 73, aspirate the manganese ion-forming compound from the third container 303, transfer the fourth nozzle 104 to the specimen preparing position 62, and discharge the manganese ion-forming compound to the cuvette 90, respectively. Steps S115 to S118 are respectively the same as Steps S107 to S110 of FIG. 3 except for a series of operations including aspirating and discharging the manganese ion-forming compound through the fourth nozzle 104. As a result, a specimen is obtained.

In the embodiment, the activator and phospholipid are added to the blood sample in this order. However, the activator and phospholipid may be simultaneously added thereto.

[Operation Procedures of Adding Calcium Salt to Specimen and Obtaining Optical Information]

Subsequently, an overview of procedures of adding a calcium salt to a specimen by the measurement device 10 and obtaining optical information will be described with reference to FIG. 5.

Figure 5:
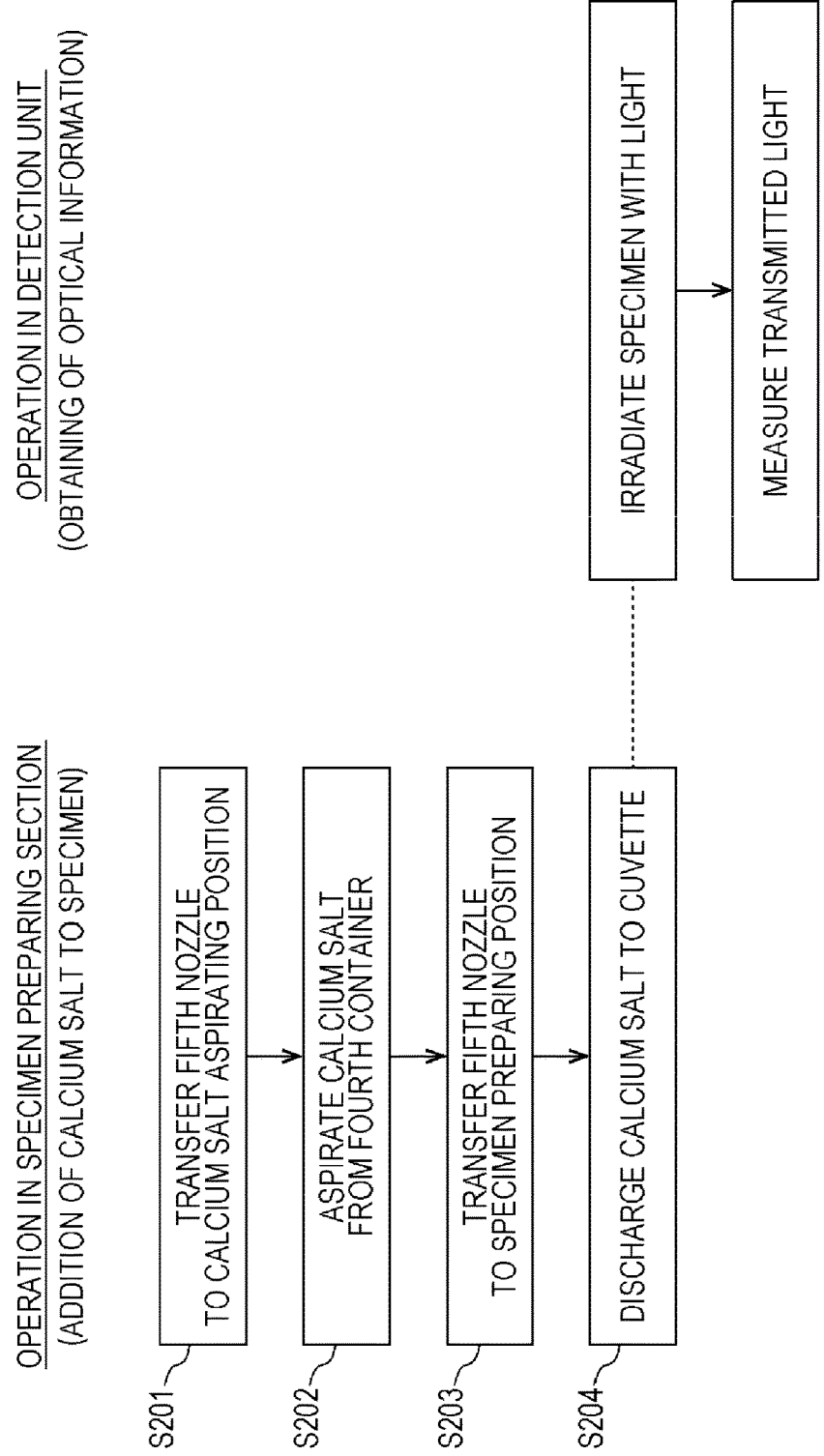
FIG. 5 is a flow chart showing procedures of adding a calcium salt to a specimen and obtaining optical information.

In Steps S201 to S204 of FIG. 5, the controller 500 makes the specimen preparing section 100 transfer the fifth nozzle 105 to a calcium salt aspirating position 74, aspirate the calcium salt from the second container 302, transfer the fifth nozzle 105 to the specimen preparing position 62, and discharge the calcium salt to the cuvette 90, respectively. As a result, a measurement specimen is obtained. Steps S201 to S204 are respectively the same as Steps S107 to S110 of FIG. 3 except for a series of operations including aspirating and discharging the calcium salt through the fifth nozzle 105.

In Step S301, simultaneously with Step S204, the controller 500 makes the specimen preparing section 100 transfer the cuvette 90 to the second cuvette mounting portion 203 of the detection unit 200 through the cuvette transporting section 131. In Step S301, the controller 500 makes the detection unit 200 irradiate the measurement specimen with light. Specifically, the controller 500 makes the light irradiation unit 201 of the detection unit 200 emit light to the cuvette 90 mounted in the second cuvette mounting portion 203. As a result, the measurement specimen in the cuvette 90 is irradiated with light.

Then, in Step 302, the controller 500 makes the detection unit 200 measure the light from the measurement specimen. Specifically, the controller 500 makes the calculator 31 of the processing apparatus 30 output an electric signal corresponding to the amount of the transmitted light received by the light receiver 202 of the detection unit 200.

Figure 2:
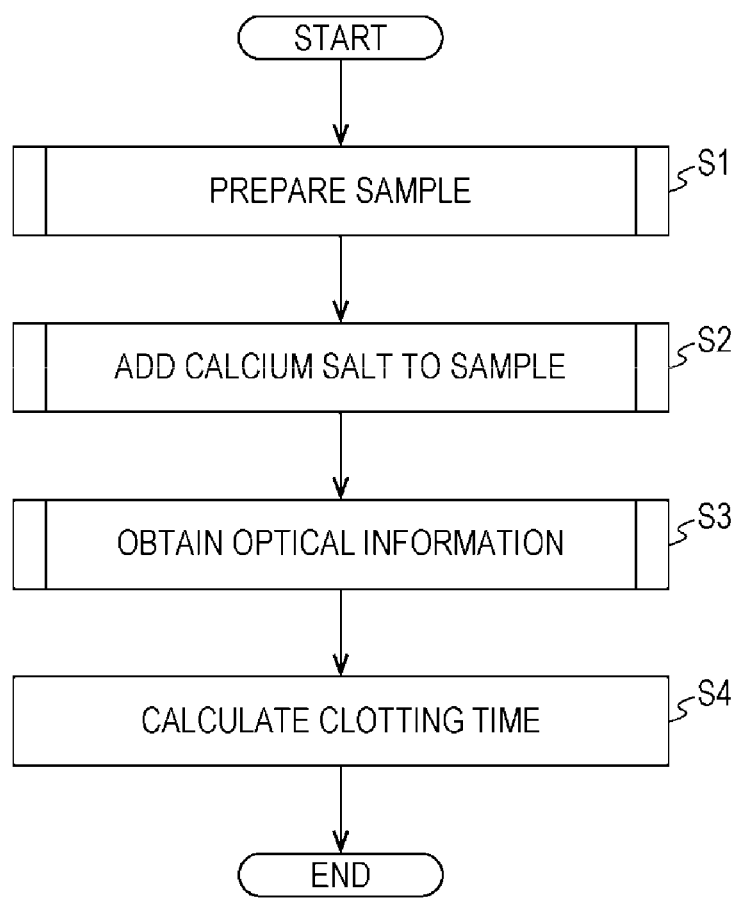
FIG. 2 is a flow chart showing a procedure of measuring the clotting time with a measurement device.

Thereafter, the process proceeds to the calculation of clotting time in Step S4 of FIG. 2.

[Modification of Operation Procedures]

A series of Steps S107 to S110 may be performed in conjunction with a series of Steps S111 to S114. A series of Steps S115 to S118 may be performed before both of the series of Steps S107 to S110 and the series of Steps S111 to S114.

When the clotting time is measured based on the increase in the viscosity due to blood clotting, one usable as the detection unit 200 is a detection unit that includes a high frequency transmitting coil, a high frequency receiving coil, a cuvette mounting portion on which a cuvette accommodating a steel ball is mounted, and an electromagnet. Here, the controller 500 makes the detection unit 200 detect changes in amplitude based on reception of a high-frequency wave transmitted by the high frequency transmitting coil of the detection unit 200 by the high frequency receiving coil. Then, the controller 500 makes the processing apparatus 30 output information on changes in amplitude detected by the detection unit 200. Thereafter, the calculator 31 of the processing apparatus 30 uses the obtained information on changes in amplitude and executes the computer program for measuring clotting time which is stored in the storage unit 602 to calculate the clotting time.

3. Clotting Time Measuring Reagent

The clotting time measuring reagent according to the embodiment is a clotting time measuring reagent used in the method for measuring a clotting time which contains a manganese ion-forming compound. The manganese ion-forming compound is the same as the manganese ion-forming compound in the measurement method.

The clotting time measuring reagent according to the embodiment may be a reagent that is substantially formed of a manganese ion-forming compound, or a reagent that contains a manganese ion-forming compound, an appropriate solvent, and further an adjuvant. The clotting time measuring reagent according to the embodiment does not substantially contain a phospholipid and an activator.

The clotting time measuring reagent may be provided in a solid state. In this case, examples of dosage forms of the clotting time measuring reagent include granules and dust formulations, but are not particularly limited thereto.

The clotting time measuring reagent may be in a state where the manganese ion-forming compound is dissolved in an appropriate solvent. In this case, examples of the solvent include desalinated and purified water and physiological saline, but are not particularly limited thereto.

When the clotting time measuring reagent is a reagent in a state where the manganese ion-forming compound is dissolved in an appropriate solvent, the content of the manganese ion-forming compound in the clotting time measuring reagent is preferably 1 $\mu$M or more, more preferably 0.1 mM or more, and preferably 50 mM or less, more preferably 10 mM or less.

When the clotting time measuring reagent further contains an adjuvant, examples of the adjuvant include a stabilizer and a preservative for the manganese ion-forming compound, but are not particularly limited thereto.

4. Reagent Kit

Figure 6:
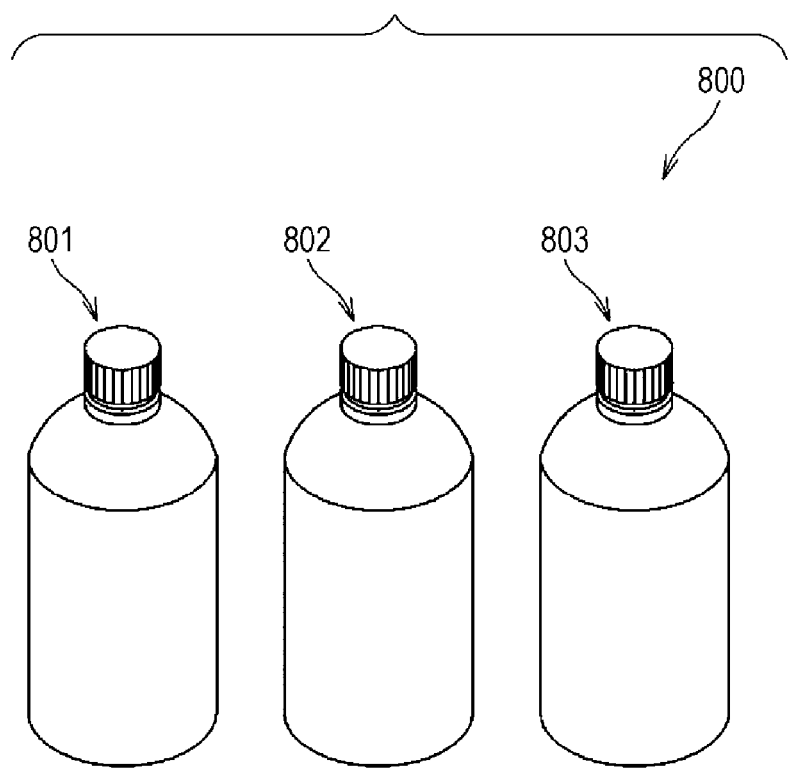
FIG. 6 is a configuration diagram of a reagent kit.

The reagent kit according to the embodiment is a reagent kit including a first reagent containing an activator and a phospholipid accommodated in a first reagent container, a second reagent containing a manganese ion-forming compound accommodated in a second reagent container, and a third reagent containing a calcium salt accommodated in a third reagent container. An example of the reagent kit according to the embodiment is a reagent kit 800 shown in FIG. 6, but is not particularly limited thereto. The reagent kit 800 shown in FIG. 6 includes a first reagent container 801, a second reagent container 802, and a third reagent container 803. The first reagent container 801 accommodates the first reagent containing an activator and a phospholipid. The second reagent container 802 accommodates the second reagent containing a manganese ion-forming compound. The third reagent container 803 accommodates the third reagent containing a calcium salt. The reagent kit may further include a package insert. The package insert may include the description of a procedure to perform the method for measuring a clotting time using the reagent kit according to the embodiment.

The concentration of the activator in the first reagent should be within a range in which the concentration in the measurement specimen can be adjusted in the range of the concentration in the measurement method. When the activator is an ellagic acid compound, usually, the concentration of the activator in the first reagent is preferably from 10 to 400 $\mu$M and more preferably from 50 to 150 $\mu$M. When the activator is silica, usually, the concentration of the activator in the first reagent is preferably from 0.1 to 1 mg/mL and more preferably from 0.2 to 0.6 mg/mL.

The concentration of the phospholipid in the first reagent should be within a range in which the concentration in the measurement specimen can be adjusted in the range of the concentration in the measurement method. Usually, the concentration of the phospholipid in the first reagent is preferably from 30 to 400 $\mu$g/mL and more preferably from 10 to 100 $\mu$g/mL. When the phospholipid is phosphatidylethanolamine, usually, the concentration of the phospholipid in the first reagent is preferably from 10 to 100 $\mu$g/mL and more preferably from 20 to 50 $\mu$g/mL. When the phospholipid is phosphatidylcholine, usually, the concentration of the phospholipid in the measurement specimen is preferably from 10 to 300 $\mu$g/mL and more preferably from 10 to 100 $\mu$g/mL. When the phospholipid is phosphatidylserine, usually, the concentration of the phospholipid in the measurement specimen is preferably from 1 to 75 $\mu$g/mL and more preferably from 2 to 15 $\mu$g/mL.

The second reagent may be a manganese ion-forming compound in a solid state, or may be in a state where a manganese ion-forming compound is dissolved in an appropriate solvent. The solvent is the same as the solvent in the clotting time measuring reagent.

When the second reagent is a reagent in a state where a manganese ion-forming compound is dissolved in an appropriate solvent, the concentration of the manganese ion-forming compound in the second reagent and the concentration of the phospholipid in the first reagent should be within a range in which the concentration in the measurement specimen can be adjusted in the range of the concentration in the measurement method. In this case, the concentration of the manganese ion-forming compound in the second reagent is preferably 1 µM or more, more preferably 0.1 mM or more, and preferably 50 mM or less, more preferably 10 mM or less.

The concentration of the calcium salt in the third reagent should be within a range in which the concentration in the measurement specimen can be adjusted in the range of the concentration in the measurement method. The concentration of the calcium salt in the third reagent is preferably from 2.5 to 40 mM and more preferably from 10 to 30 mM.

In the reagent kit according to the embodiment, the second reagent does not substantially contain the phospholipid and activator. In the reagent kit according to the embodiment, the first reagent does not substantially contain the manganese ion-forming compound.

The activator, phospholipid, manganese ion-forming compound, and calcium salt used in the reagent kit are the same as those used in the measurement method. Each of the reagent containers may accommodate an appropriate solvent, an adjuvant or the like, if appropriate. The solvent and adjuvant are the same as the solvent and reagent used in the clotting time measuring reagent. In the reagent kit according to the embodiment, the activator and phospholipid may be accommodated in separate containers.

EXAMPLES

The clotting time was measured with a fully automated clotting time measurement device (product name: CS-2000i, manufactured by Sysmex Corporation).

Example 1

In this example, normal plasma, test plasma or pooled plasma (with a volume ratio of test plasma/normal plasma of 1:1) was used as a blood sample. The used normal plasma is the normal plasma shown in Table 1. The used test plasma includes plasma from an LA-positive patient shown in Table 1, heparin-containing plasma shown in Table 2, and plasma from a patient with coagulation factor VIII deficiency and plasma from a patient with coagulation factor IX deficiency shown in Table 3. In Table 3, "PNP" is an abbreviation for Pooled Normal Plasma.

TABLE 1

| Blood sample | | | | |
|---|---|---|---|---|
| Normal plasma | | Pooled Normal Plasma (PBI) | Lot. A1156, manufactured by Precision BioLogic Incorporated | |
| Plasma from LA-positive patient | LA1 | Weak Lupus Positive Control | Lot. WL-022, manufactured by Precision BioLogic Incorporated | Mixed with Pooled Normal Plasma (PBI) at 1:1 |
| Plasma from LA-positive patient | LA2 | Weak Lupus Positive Control | Lot. WL-022, manufactured by Precision BioLogic Incorporated | |
| Plasma from LA-positive patient | LA3 | Lupus Positive Control | Lot. 6246, manufactured by Precision BioLogic Incorporated | Mixed with Pooled Normal Plasma (PBI) at 1:1 |
| Plasma from LA-positive patient | LA4 | Lupus Positive Control | Lot. 6246, manufactured by Precision BioLogic Incorporated | |
| Plasma from LA-positive patient | LA5 | Weak Lupus Positive Control | Lot. WL-023, manufactured by Precision BioLogic Incorporated | Mixed with Pooled Normal Plasma (PBI) at 1:1 |
| Plasma from LA-positive patient | LA6 | Weak Lupus Positive Control | Lot. WL-023, manufactured by Precision BioLogic Incorporated | |
| Plasma from LA-positive patient | LA7 | Lupus Positive Control | Lot. 6248, manufactured by Precision BioLogic Incorporated | Mixed with Pooled Normal Plasma (PBI) at 1:1 |
| Plasma from LA-positive patient | LA8 | Lupus Positive Control | Lot. 6248, manufactured by Precision BioLogic Incorporated | |
| Plasma from LA-positive patient | LA9 | George King LA Positive | Lot. GK5003-1312, manufactured by George King Bio-Medical, Inc. | Mixed with Pooled Normal Plasma (PBI) at 1:1 |
| Plasma from LA-positive patient | LA10 | George King LA Positive | Lot. GK5003-1312, manufactured by George King Bio-Medical, Inc. | |
| Plasma from LA-positive patient | LA11 | LA Control Low | Lot. 54604322, manufactured by Siemens Healthcare K.K. | Mixed with Pooled Normal Plasma (PBI) at 1:1 |
| Plasma from LA-positive patient | LA12 | LA Control Low | Lot. 54604322, manufactured by Siemens Healthcare K.K. | |
| Plasma from LA-positive patient | LA13 | LA Control High | Lot. 545918A, manufactured by Siemens Healthcare K.K. | Mixed with Pooled Normal Plasma (PBI) at 1:1 |
| Plasma from LA-positive patient | LA14 | LA Control High | Lot. 545918A, manufactured by Siemens Healthcare K.K. | |

TABLE 2

| Blood sample | | | | |
|---|---|---|---|---|
| Heparin-containing plasma | HE1 | Sample containing 0.1 U/mL novo heparin | Addition of novo heparin to control plasma (product name: Coagtrol Lot. 022, manufactured by Sysmex Corporation) | Mixed with Pooled Normal Plasma (PBI) at 1:1 |
| Heparin-containing plasma | HE2 | Sample containing 0.1 U/mL novo heparin | Addition of novo heparin to control plasma (product name: Coagtrol Lot. 022, manufactured by Sysmex Corporation) | |
| Heparin-containing plasma | HE3 | Sample containing 0.2 U/mL novo heparin | Addition of novo heparin to control plasma (product name: Coagtrol Lot. 022, manufactured by Sysmex Corporation) | Mixed with Pooled Normal Plasma (PBI) at 1:1 |
| Heparin-containing plasma | HE4 | Sample containing 0.2 U/mL novo heparin | Addition of novo heparin to control plasma (product name: Coagtrol Lot. 022, manufactured by Sysmex Corporation) | |

TABLE 2-continued

| Blood sample | | | | |
|---|---|---|---|---|
| Heparin-containing plasma | HE5 | Sample containing 0.3 U/mL novo heparin | Addition of novo heparin to control plasma (product name: Coagtrol Lot. 022, manufactured by Sysmex Corporation) | Mixed with Pooled Normal Plasma (PBI) at 1:1 |
| Heparin-containing plasma | HE6 | Sample containing 0.3 U/mL novo heparin | Addition of novo heparin to control plasma (product name: Coagtrol Lot. 022, manufactured by Sysmex Corporation) | |
| Heparin-containing plasma | HE7 | Sample containing 0.4 U/mL novo heparin | Addition of novo heparin to control plasma (product name: Coagtrol Lot. 022, manufactured by Sysmex Corporation) | Mixed with Pooled Normal Plasma (PBI) at 1:1 |
| Heparin-containing plasma | HE8 | Sample containing 0.4 U/mL novo heparin | Addition of novo heparin to control plasma (product name: Coagtrol Lot. 022, manufactured by Sysmex Corporation) | |
| Heparin-containing plasma | HE9 | Sample containing 0.6 U/mL novo heparin | Addition of novo heparin to control plasma (product name: Coagtrol Lot. 022, manufactured by Sysmex Corporation) | Mixed with Pooled Normal Plasma (PBI) at 1:1 |
| Heparin-containing plasma | HE10 | Sample containing 0.6 U/mL novo heparin | Addition of novo heparin to control plasma (product name: Coagtrol Lot. 022, manufactured by Sysmex Corporation) | |

TABLE 3

| Blood sample | | | | |
|---|---|---|---|---|
| Plasma from patient with coagulation factor VIII deficiency | FVIII1 | FVIII-deficient sample | Mixture of 80% by volume of FVIII def Lot. 546593 (product name) with 20% by volume of PNP, manufactured by Siemens Healthcare K.K. | Mixed with Pooled Normal Plasma (PBI) at 1:1 |
| Plasma from patient with coagulation factor VIII deficiency | FVIII2 | FVIII-deficient sample | Mixture of 80% by volume of FVIII def Lot. 546593 (product name) with 20% by volume of PNP, manufactured by Siemens Healthcare K.K. | |
| Plasma from patient with coagulation factor VIII deficiency | FVIII3 | FVIII-deficient sample | Mixture of 90% by volume of FVIII def Lot. 546593 (product name) with 10% by volume of PNP, manufactured by Siemens Healthcare K.K. | Mixed with Pooled Normal Plasma (PBI) at 1:1 |
| Plasma from patient with coagulation factor VIII deficiency | FVIII4 | FVIII-deficient sample | Mixture of 90% by volume of FVIII def Lot. 546593 (product name) with 10% by volume of PNP, manufactured by Siemens Healthcare K.K. | |
| Plasma from patient with coagulation factor VIII deficiency | FVIII5 | FVIII-deficient sample | Mixture of 95% by volume of FVIII def Lot. 546593 (product name) with 5% by volume of PNP, manufactured by Siemens Healthcare K.K. | Mixed with Pooled Normal Plasma (PBI) at 1:1 |
| Plasma from patient with coagulation factor VIII deficiency | FVIII6 | FVIII-deficient sample | Mixture of 95% by volume of FVIII def Lot. 546593 (product name) with 5% by volume of PNP, manufactured by Siemens Healthcare K.K. | |
| Plasma from patient with coagulation factor VIII deficiency | FVIII7 | FVIII-deficient sample | Mixture of 99% by volume of FVIII def Lot. 546593 (product name) with 1% by volume of PNP, manufactured by Siemens Healthcare K.K. | Mixed with Pooled Normal Plasma (PBI) at 1:1 |
| Plasma from patient with coagulation factor VIII deficiency | FVIII8 | FVIII-deficient sample | Mixture of 99% by volume of FVIII def Lot. 546593 (product name) with 1% by volume of PNP, manufactured by Siemens Healthcare K.K. | |
| Plasma from patient with coagulation factor IX deficiency | FIX1 | FIX-deficient sample | Mixture of 80% by volume of FIX def Lot. 500871A (product name) with 20% by volume of PNP, manufactured by Siemens Healthcare K.K. | Mixed with Pooled Normal Plasma (PBI) at 1:1 |
| Plasma from patient with coagulation factor IX deficiency | FIX2 | FIX-deficient sample | Mixture of 80% by volume of FIX def Lot. 500871A (product name) with 20% by volume of PNP, manufactured by Siemens Healthcare K.K. | |
| Plasma from patient with coagulation factor IX deficiency | FIX3 | FIX-deficient sample | Mixture of 90% by volume of FIX def Lot. 500871A (product name) with 10% by volume of PNP, manufactured by Siemens Healthcare K.K. | Mixed with Pooled Normal Plasma (PBI) at 1:1 |
| Plasma from patient with coagulation factor IX deficiency | FIX4 | FIX-deficient sample | Mixture of 90% by volume of FIX def Lot. 500871A (product name) with 10% by volume of PNP, manufactured by Siemens Healthcare K.K. | |
| Plasma from patient with coagulation factor IX deficiency | FIX5 | FIX-deficient sample | Mixture of 95% by volume of FIX def Lot. 500871A (product name) with 5% by volume of PNP, manufactured by Siemens Healthcare K.K. | Mixed with Pooled Normal Plasma (PBI) at 1:1 |

TABLE 3-continued

| Blood sample | | | | |
|---|---|---|---|---|
| Plasma from patient with coagulation factor IX deficiency | FIX6 | FIX-deficient sample | Mixture of 95% by volume of FIX def Lot. 500871A (product name) with 5% by volume of PNP, manufactured by Siemens Healthcare K.K. | |
| Plasma from patient with coagulation factor IX deficiency | FIX7 | FIX-deficient sample | Mixture of 99% by volume of FIX def Lot. 500871A (product name) with 1% by volume of PNP, manufactured by Siemens Healthcare K.K. | Mixed with Pooled Normal Plasma (PBI) at 1:1 |
| Plasma from patient with coagulation factor IX deficiency | FIX8 | FIX-deficient sample | Mixture of 99% by volume of FIX def Lot. 500871A (product name) with 1% by volume of PNP, manufactured by Siemens Healthcare K.K. | |

First, 50 μL of a blood sample was heated at 37° C. for 60 seconds. Then, 50 μL of an APTT reagent (product name: PTT-LA (registered trademark), manufactured by Roche Diagnostics K.K.) was added to the heated blood sample and mixed therewith. The obtained mixture was heated at 37° C. for 20 seconds. Then, 20 μL of a 2.5 mM aqueous manganese chloride solution was added to the heated mixture and mixed therewith. The obtained mixture was heated at 37° C. for 170 seconds. As a clotting reaction accelerator, a 25 mM aqueous calcium chloride solution was added to the heated mixture, and the clotting time of the obtained measurement specimen was measured.

The obtained clotting times were used to calculate the index of circulating anticoagulant (ICA). The ICA value was calculated in accordance with the following formula (I):

$$ICA = [(D-A)/G] \times 100 \quad (I),$$

wherein A represents the clotting time of normal plasma, and D represents the clotting time of pooled plasma (with a volume ratio of test plasma/normal plasma of 1:1).

Figure 7:
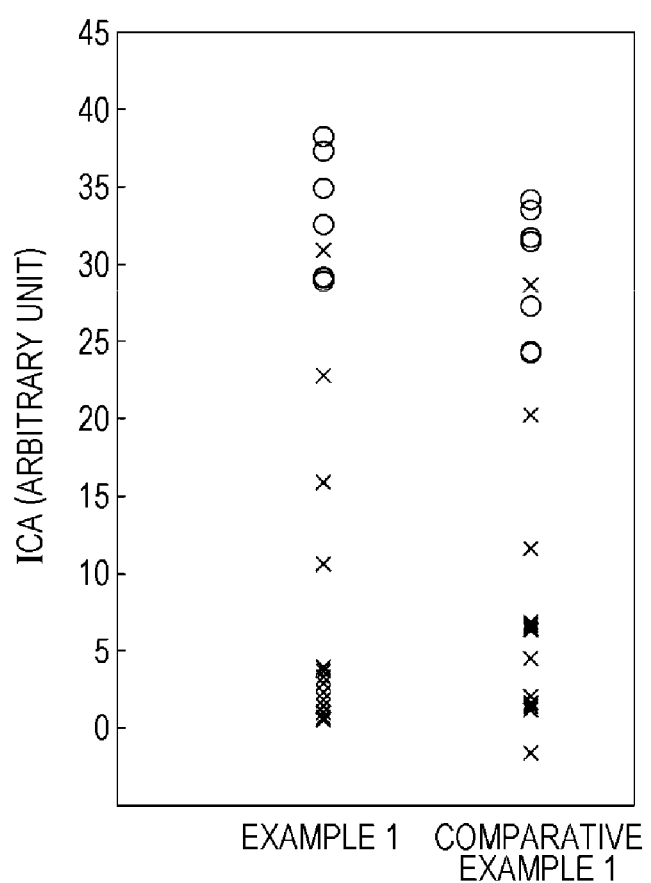
FIG. 7 is a graph showing results of examined ICA values in Example 1 and Comparative Example 1.

The ICA values obtained by the measurement method of Example 1 are shown in FIG. 7. In the graph, a white circle represents an ICA value of plasma from an LA-positive patient, and a cross represents an ICA value of plasma other than the plasma from an LA-positive patient. The term "plasma other than the plasma from an LA-positive patient" means heparin-containing plasma, plasma from a patient with coagulation factor VIII deficiency, and plasma from a patient with coagulation factor IX deficiency.

Comparative Example 1

In this comparative example, the used blood sample is the same blood sample as in Example 1. First, 50 μL of the blood sample was heated at 37° C. for 60 seconds. Then, 50 μL of an APTT reagent (product name: PTT-LA (registered trademark), manufactured by Roche Diagnostics K.K.) was added to the heated blood sample and mixed therewith. The obtained mixture was heated at 37° C. for 170 seconds. A 25 mM aqueous calcium chloride solution was added to the heated mixture and the clotting time of the obtained measurement specimen was measured.

The obtained clotting times were used to calculate the ICA value in accordance with formula (I). The ICA values obtained by the measurement method of Comparative Example 1 are shown in FIG. 7. In the graph, a white circle represents an ICA value of plasma from an LA-positive patient, and a cross represents an ICA value of plasma other than the plasma from an LA-positive patient.
(Results)

The results in FIG. 7 show that the ICA values of plasma from an LA-positive patient are concentrated in the range of 28 to 39 in the case of the measurement method of Example 1, whereas the ICA values of plasma other than the plasma from an LA-positive patient are concentrated in the range of 0 to 24 in the case of the measurement method of Comparative Example 1. Therefore, it is found that the measurement method of Example 1 can distinguish between plasma from an LA-positive patient and plasma other than the plasma from an LA-positive patient.

The results in FIG. 7 show that the ICA values obtained by the measurement method of Example 1 are generally higher than the ICA values obtained by the measurement method of Comparative Example 1. Therefore, it is found that the measurement method of Example 1 can detect the plasma from an LA-positive patient at higher sensitivity, compared to the measurement method of Comparative Example 1.

Example 2

The operation was performed in the same manner as in Example 1 except that normal plasma was used as a blood sample, and then the clotting time was measured. Clotting times measured by the measurement method of Example 2 are shown in FIG. 8.

Comparative Example 2

The operation was performed in the same manner as in Comparative Example 1 except that normal plasma was used as a blood sample, and then the clotting time was measured. Clotting times measured by the measurement method of Comparative Example 2 are shown in FIG. 8.
(Results)

Figure 8:
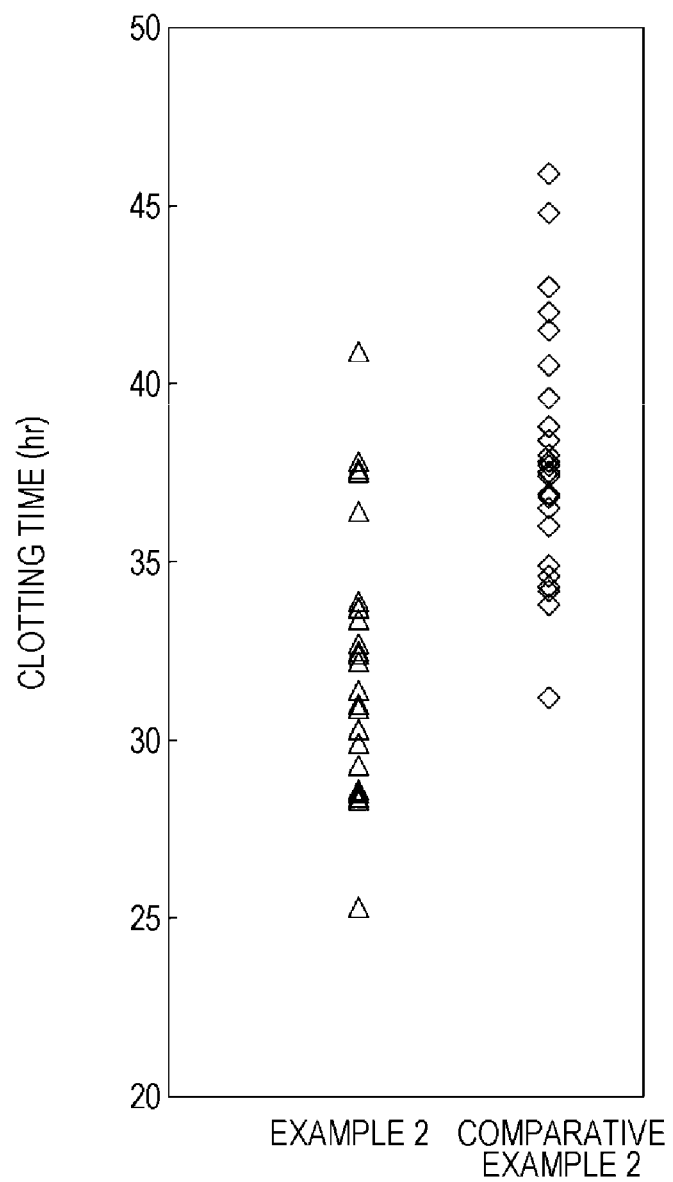
FIG. 8 is a graph showing results of examined clotting time in Example 2 and Comparative Example 2.

The results in FIG. 8 show that the clotting time obtained by the measurement method of Example 2 is generally shorter than the clotting time measured by the measurement method of Comparative Example 2. Therefore, it is found that, in the clotting time measurement using the APTT reagent, a manganese ion-forming compound is added to a blood sample before addition of a clotting reaction accelerator, whereby excessive prolongation of the clotting time can be prevented.

What is claimed is:
1. A method for measuring a clotting time, comprising:
a mixing step of mixing a blood sample, an activator for causing activation of the intrinsic coagulation pathway and selected from the group consisting of ellagic acid compounds, silica, kaolin, and diatomaceous earth, a phospholipid, and a manganese ion-forming compound to obtain a specimen; and
a measurement step of mixing the specimen obtained in the mixing step with a calcium salt to prepare a measurement specimen and measuring the clotting time of the measurement specimen, wherein the blood sample is mixed with the manganese ion-forming compound separately from the activator and the phospholipid in the mixing step.

2. The method according to claim 1, wherein the mixing step includes the steps of:
   (A) mixing the blood sample, the activator, and the phospholipid to obtain a mixture; and
   (B) mixing the mixture with the manganese ion-forming compound.

3. The method according to claim 2, wherein the manganese ion-forming compound is mixed with the mixture in step (B) within 150 seconds after end of mixing the blood sample, the activator, and the phospholipid in step (A).

4. The method according to claim 1, wherein the manganese ion-forming compound in the measurement specimen has a final concentration of 0.1 μM or more and less than 10 mM.

5. The method according to claim 1, wherein the manganese ion-forming compound in the measurement specimen has a final concentration of 0.1 mM or more and less than 5 mM.

6. The method according to claim 1, wherein, in the measurement step, the measurement specimen is incubated at a temperature of 30° C. or more and 45° C. or less, and then the calcium salt is mixed with the measurement specimen.

7. The method according to claim 1, wherein, in the measurement step, the measurement specimen is incubated at a temperature of 36° C. or more and 38° C. or less, and then the calcium salt is mixed with the measurement specimen.

8. The method according to claim 1, wherein, in the measurement step, the measurement specimen is incubated for 1 minutes or more and 6 minutes or less, and then the calcium salt is mixed with the measurement specimen.

9. The method according to claim 1, wherein, in the measurement step, the measurement specimen is incubated for 2 minutes or more and 5 minutes or less, and then the calcium salt is mixed with the measurement specimen.

10. The method according to claim 1, wherein, in the measurement step, the measurement specimen is incubated at a temperature of 36° C. or more and 38° C. or less for 2 minutes or more and 5 minutes or less, and then the calcium salt is mixed with the measurement specimen.

11. The method according to claim 1, wherein the manganese ion-forming compound is a compound that forms a divalent ion.

12. The method according to claim 1, wherein the manganese ion-forming compound is a compound selected from the group consisting of manganese chloride, potassium permanganate, manganese sulfate, manganese nitrate, and manganese acetate.

13. A method for detecting a lupus anticoagulant in a blood sample, comprising:
    the method for measuring a clotting time according to claim 1, and
    a detecting step of detecting a lupus anticoagulant based on the clotting time.

* * * * *